(12) United States Patent
Van Leeuwen et al.

(10) Patent No.: US 11,887,355 B2
(45) Date of Patent: Jan. 30, 2024

(54) SYSTEM AND METHOD FOR ANALYSIS OF MICROSCOPIC IMAGE DATA AND FOR GENERATING AN ANNOTATED DATA SET FOR CLASSIFIER TRAINING

(71) Applicant: KONINKLIJKE PHILIPS N.V., Eindhoven (NL)

(72) Inventors: Marinus Bastiaan Van Leeuwen, Eindhoven (NL); Ruud Vlutters, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 317 days.

(21) Appl. No.: 17/267,819

(22) PCT Filed: Aug. 15, 2019

(86) PCT No.: PCT/EP2019/071890
§ 371 (c)(1),
(2) Date: Feb. 11, 2021

(87) PCT Pub. No.: WO2020/035550
PCT Pub. Date: Feb. 20, 2020

(65) Prior Publication Data
US 2021/0166076 A1 Jun. 3, 2021

(30) Foreign Application Priority Data
Aug. 15, 2018 (EP) .................................. 18189091

(51) Int. Cl.
*G06K 9/00* (2022.01)
*G06V 10/774* (2022.01)
(Continued)

(52) U.S. Cl.
CPC ............ *G06V 10/774* (2022.01); *G06F 16/55* (2019.01); *G06F 18/2148* (2023.01);
(Continued)

(58) Field of Classification Search
CPC .... G06V 10/774; G06V 20/69; G06V 20/698; G06V 2201/03; G06F 16/55;
(Continued)

(56) References Cited

U.S. PATENT DOCUMENTS

2016/0335478 A1 11/2016 Bredno
2017/0161891 A1 6/2017 Madabhushi

FOREIGN PATENT DOCUMENTS

WO WO-2018005413 A1 * 1/2018 ........... G06K 9/0014
WO WO2018005413 A1 1/2018

OTHER PUBLICATIONS

Christoph Sommer, Learning-based mitotic cell detection in histopathological images, 21st International Conference on Pattern Recognition.*

(Continued)

*Primary Examiner* — Xin Jia
(74) *Attorney, Agent, or Firm* — Sherry Austin

(57) ABSTRACT

Disclosed is a system for analysis of microscopic image data which includes a data processing system. Pixel classification data for each of a plurality of pixels of the microscopic image data are read. The pixel classification data include for each of the pixels of the microscopic image data, binary or probabilistic classification data for classifying the pixel of the microscopic image data into one or more object classes of pre-defined objects which are shown by the image. At least a portion of the pixels of the microscopic image data are grouped to form one or more pixels groups. For each of the pixel groups, probabilistic group classificati on data are calculated depending on the pixel classification data of the pixels of the respective group. The probabilistic group classification data are indicative of a probability that the group shows at least a portion of an object of the respective object class.

19 Claims, 5 Drawing Sheets

(51) Int. Cl.
  *G16H 30/20* (2018.01)
  *G16H 30/40* (2018.01)
  *G06F 16/55* (2019.01)
  *G06N 3/04* (2023.01)
  *G06N 3/08* (2023.01)
  *G06V 20/69* (2022.01)
  *G06F 18/214* (2023.01)
  *G06F 18/40* (2023.01)
  *G06F 18/232* (2023.01)
  *G06F 18/2415* (2023.01)

(52) U.S. Cl.
  CPC ........ *G06F 18/232* (2023.01); *G06F 18/2415* (2023.01); *G06F 18/40* (2023.01); *G06N 3/04* (2013.01); *G06N 3/08* (2013.01); *G06V 20/69* (2022.01); *G06V 20/698* (2022.01); *G16H 30/20* (2018.01); *G16H 30/40* (2018.01); *G06V 2201/03* (2022.01)

(58) Field of Classification Search
  CPC .............. G06F 18/2148; G06F 18/232; G06F 18/2415; G06F 18/40; G06N 3/04; G06N 3/08; G06N 3/045; G16H 30/20; G16H 30/40; G06T 2207/10056; G06T 2207/20081; G06T 2207/20084; G06T 2207/30024
  See application file for complete search history.

(56) References Cited

OTHER PUBLICATIONS

David J. Logan, Quantifying co-cultured cell phenotypes in high-throughput using pixel-based classification, ScienceDirect.*

PCT International Search Report, International application No. PCT/EP2019/071890, dated Oct. 22, 2019.

Chowdhury A. et al., "Active Deep Learning Reduces Annotation Burden in Automatic Cell Segmentation", bioRxiV, Nov. 1, 2017 (Nov. 1, 2017), XP055547750.

Veta M. et al., "Assessment of Algorithms for Mitosis Detection in Breast Cancer Histopathology Images", Medical Image Analysis 20 (2015) 237-248.

Sommer C. et al., "Learning-Based Mitotic Cell Detection in Histopathological Images", International Conference on Pattern Recognition, Nov. 1, 2012 (Nov. 1, 2012), pp. 2306-2309, XP055547556.

Logan D.J. et al., "Quantifying Co-Cultured Cell Phenotypes in High-Throughput Using Pixel-Based Classification", Methods, vol. 96, Mar. 1, 2016 (Mar. 1, 2016), pp. 6-11, XP055547519.

Paeng K. et al., "A Unified Framework for Tumor Proliferation Score Prediction in Breast Histopathology", 3rd Workshop on Deep Learning in Medical Image Analysis (DLMIA 2017), MICCAI 2017, Computer Vision and Pattern Recognition (cs.CV).

* cited by examiner

SYSTEM AND METHOD FOR ANALYSIS OF MICROSCOPIC IMAGE DATA AND FOR GENERATING AN ANNOTATED DATA SET FOR CLASSIFIER TRAINING

CROSS-REFERENCE TO RELATED APPLICATIONS

This patent application claims the priority benefit under 35 U.S.C. § 371 of International Patent Application no. PCT/EP2019/071890, filed Aug. 15, 2019, which claims the benefit of European Patent Application No. EP18189091.4, filed on Aug. 15, 2018. These applications are hereby incorporated by reference herein in their entirety.

FIELD OF THE INVENTION

The present invention relates to a method and a system for analysis of microscopic data. Specifically, the present invention relates to a method and a system for training a machine learning system for achieving improved recognition accuracy in analyzing histological or cytological samples.

BACKGROUND OF THE INVENTION

Tissue pathology is a cornerstone in cancer diagnosis and prognosis. In conventional techniques of cancer diagnosis and prognosis, pathologists visually review stained slides of cancer biopsy samples and assign scores to the detected tumors. This process, however, is time-consuming and the results are often inconsistent across pathologists.

Computer-assisted quantitative analysis of stained histology images have been made particularly efficient through whole slide scanners which allow acquisition of high resolution digital scans of entire microscope slides. Such scanners can rapidly generate ultra-large 2D images of a whole tissue sample for digitization of histological slides. Automatic image processing procedures can then be applied to extract structures of interest from the original image for use in diagnosis or prognosis. This area has become widely known as digital pathology and replaces manual subjective and time-consuming scoring of data by traditional pathologist assessment. The image processing procedures can automatically detect cells and tissue types and have become very powerful with the aid of deep convolutional neural network technology.

However, it has been shown that the process for acquiring annotated data sets for training the convolutional neural networks is time-consuming and cumbersome, since today's nucleus detection algorithms typically require a large number of nucleus annotations ranging approximately between 10,000 and 100,000. Further, it has been shown that the result of the training process strongly depends on the user who prepares the labelled data set used for the training process.

Therefore, a need exists for systems and methods which provide more efficient data analysis for images acquired from cells.

SUMMARY OF THE INVENTION

Embodiments of the present disclosure provide a system for analysis of microscopic image data. The system includes a data processing system which is configured to read and/or generate pixel classification data for each of a plurality of pixels of the microscopic image data. The pixel classification data include, for each of the plurality of pixels of the microscopic image data, binary or probabilistic classification data for classifying the pixel into one or more object classes of pre-defined objects which are shown by the image. The data processing system is further configured to group at least a portion of the pixels of the microscopic image data to form one or more pixels groups. The data processing system is further configured to calculate, for each of the pixel groups, probabilistic group classification data depending on at least a portion of the pixel classification data of the pixels of the respective group. For one or more of the object classes and for each of the pixel groups, the probabilistic group classification data are indicative of a probability that the respective group shows at least a portion of an object of the respective object class.

The data processing system may include a computer system having a processor and a memory for storing instructions processable by the processor. The processor may execute an operating system. The data processing system may further include a user interface configured to allow a user to receive data from the data processing system and/or to provide data to the data processing system. The user interface may include a graphical user interface.

Additionally or alternatively, the system may include an image acquisition unit for acquiring the microscopic data. The image acquisition unit may include a microscope.

The microscope may be operable at a magnification of at least 5 or at least 10. The magnification may be less than 500 or less than 200. The microscope may be a scanner, in particular a microscope slide scanner, such as a whole slide scanner. The microscope may be configured for transmission and/or reflectance imaging.

The microscopic image data may include greyscale image data and/or color image data. The image data may show a plurality of cells. The image data may have a resolution sufficient to determine the position and/or the shape of a cell nucleus having a diameter of 5 micrometers.

The pixel classification data may be generated using a classifier. The classifier may be executed by the data processing system. Alternatively, at least a portion of the operations of the classifier may be executed using second data processing system. The classifier may be a trainable classifier. The classifier may include an artificial neural network, in particular a convolutional neural network, such as a deep convolutional neural network. The artificial neural network may include a plurality of layers. The plurality of layers may include an input layer, one or more intermediate layers and an output layer. The input layer may be configured to receive input data, such as the microscopic data. The term "convolutional neural network" may be defined herein as an artificial neural network having at least one convolutional layer.

The pixel classification data may be generated depending on data outputted from a layer of the artificial neural network. The layer may be an output layer (i.e. a last layer) of the artificial neural network. Alternatively, the layer may be a layer which precedes the output layer, in particular, which immediately precedes the output layer. The output layer may implement a softmax operation. The pixel classification data may be generated using a logit function (also denoted as the inverse of the sigmoid function). The logit function may be applied to the output data of the artificial neural network and/or to data generated depending on the output data. Additionally or alternatively, the pixel classification data may be clipped and/or mapped, in particular linearly mapped, to a range of 0 to 1.

The term "probabilistic classification data" may be defined as data which include a probability value for an object class or a probability distribution for a plurality of object classes. Examples for objects are but are not limited to: a cell, a portion of a cell, such as a cell nucleus, a group of cells, such as a cell cluster, and a tissue portion. A class may relate to a cell type (such as tumor cells, tumor cell nuclei or tumor cell clusters) or a tissue type (such as tumor tissue).

A portion or all of the pixel groups may be mutually disjoint, i.e. a pixel which forms part of one of the groups is not a part of another one of the groups.

The probabilistic group classification data may include one or more probability values. Each of the probability values may be associated with one of the object classes. The probability values may cover all or a portion of the pre-defined object classes. Each of the probability values may be indicative of a probability that the pixel group shows at least a portion of an object or the whole object of the associated object class.

The data processing system may be configured to read and/or generate the microscopic image data. The data processing system may further be configured to group at least the portion of the pixels of the microscopic image data depending on at least a portion of the microscopic image data. Alternatively, it is conceivable that the data processing system groups at least the portion of the pixels of the microscopic image data without using the microscopic image data. The pixel classification data may be assigned to the pixels of the microscopic image data. Thereby, it is possible to group at least the portion of the pixels of the microscopic image data based on at least a portion of the pixel classification data, but without using the microscopic image data.

The grouping of at least the portion of the pixels of the microscopic image data to form the one or more pixel groups may include determining, for each of a plurality of pixel coordinate pairs (e.g. a horizontal pixel coordinate and its associated vertical pixel), whether or not the respective pixel coordinate pair forms part of one or more pixel groups.

According to an embodiment, the data processing system comprises a user interface which is configured for interactive generation of an annotated data set for training a classifier. The annotated data set may be generated using the pixels of the image data and the probabilistic group classification data of one or more of the pixel groups.

The term "annotated data set" may be defined as a data set which is configured to be used by a trainable classifier to train the trainable classifier. The annotated data set may include a plurality of image data sets and a classification label associated with each of the image data sets. Each of the image data sets may include the microscopic image data values of one of the pixel groups. The data processing system may be configured to store the annotated data set on a storage device and/or to output the annotated data set to an external device.

The classification label may be defined using user input received via the user interface. The classification label may assign a pixel group to one or more of the object classes and/or may indicate that the pixel group does not represent an object of any of the predefined object classes.

According to a further embodiment, the data processing system is configured to display, using a graphical user interface of the data processing system, one or more of the pixel groups and for each of the displayed pixel groups a visually perceptible indicator which is generated depending on the probabilistic group classification data of the respective pixel group.

The indicator may be overlaid over at least a portion of the image which is displayed to the user by the graphical user interface. The indicator may be indicative of at least a portion of the probabilistic group classification data. The indicator may be indicative of a value and/or a range of values of a probability value of the group probability data.

According to a further embodiment, the indicator is indicative of an extent of the respective pixel group. By way of example, the indicator may at least partially surround the pixel group. The indicator may be in the form of a loop and/or the indicator may at least partially cover the pixel group. The indicator may be configured so that the pixels of the pixel group are still visible to the user.

According to a further embodiment, the one or more pixel groups are formed depending on at least a portion of the pixel classification data. Additionally or alternatively, the data processing system may be configured to form the pixel groups depending on at least a portion of the microscopic image data.

The data processing system may be configured to perform a segmentation of the microscopic image data depending on the pixel classification data and/or depending on the microscopic image data. Data values of the microscopic image data used for the segmentation of the image may include one or a combination of: an intensity value, a parameter of color appearance, such as hue, colorfulness, saturation, lightness and brightness. The formation of the groups may be performed using one or more image processing operations on the pixel data values and/or on the pixel classification data.

According to a further embodiment, the one or more pixel groups are formed using a threshold value for the pixel classification data. The formation of at least one of the pixel groups may include comparing the pixel classification data of the pixels of the respective pixel group with the threshold value. For one or more or all of the pixel groups, a same threshold value may be used. The data processing system may be configured so that one or more of the pixel groups are selectable by the user via the user interface. The data processing system may further be configured so that for each of the selected pixel groups, the threshold value of the respective pixel group is adaptable depending on user input received via the user interface. The data processing system may then use the adapted one or more threshold values to form one or more pixel groups which replace the selected one or more pixel groups.

According to a further embodiment, for each of the pixel groups, the corresponding probabilistic group classification data are determined depending on a mean value of the pixel classification data of at least a portion of the pixels of the respective pixel group.

The mean value may be calculated using one or more algorithms selected from the group consisting of an arithmetic-geometric mean, a generalized mean, an arithmetic-harmonic mean, a geometric mean, a power mean, a harmonic-geometric mean, a pythagorean mean, an arithmetic mean, a harmonic mean, a root mean square (RMS), a Heronian mean, a Holder mean, a Stolarsky mean, an Identric mean, a Lehmer mean, a weighted mean, or a combination thereof.

According to a further embodiment, the data processing system is configured to generate the pixel classification data using a classifier and to perform supervised training of the classifier using the pixels of the microscopic image data and the probabilistic group classification data of at least a portion of the pixel groups. The classifier may be implemented in the data processing system.

According to a further embodiment, each of the pixel groups represents or substantially represents a pixel cluster. The term "pixel cluster" may be defined to mean a non-divided image region. In other words, the pixel cluster may represent a contiguous image region. Every pixel of the pixel cluster has at least one adjacent pixel which forms part of the same pixel cluster.

According to a further embodiment, the data processing system is configured to exclude, for one or more of the pixel groups, transition pixels of the microscopic image data from the determination of the probabilistic group classification data. The transition pixels may represent a transition from an interior of the respective pixel group to an image region which is adjacent to the pixel group and which is not part of a pixel group.

Embodiments of the present disclosure provide a method for analysis of microscopic image data using a data processing system. The method comprises reading and/or generating pixel classification data for each of a plurality of pixels of the microscopic image data, wherein the pixel classification data comprise, for each of the plurality of pixels of the microscopic image data, binary or probabilistic classification data for classifying the pixel into one or more object classes of pre-defined objects which are shown by the image. The method further comprises grouping at least a portion of the pixels of the microscopic image data to form one or more pixels groups. The method further comprises calculating, for each of the pixel groups, probabilistic group classification data depending on at least a portion of the pixel classification data of the pixels of the respective group. For one or more of the object classes and for each of the pixel groups, the probabilistic group classification data are indicative of a probability that the respective group shows at least a portion of an object of the respective object class.

Embodiments of the present disclosure provide a program element for analysis of microscopic image data using a data processing system. The program element, when being executed by a processor of the data processing system, is adapted to carry out reading and/or generating pixel classification data for each of a plurality of pixels of the microscopic image data. The pixel classification data comprise, for each of the plurality of pixels of the microscopic image data, binary or probabilistic classification data for classifying the pixel into one or more object classes of pre-defined objects which are shown by the image. The processor is further adapted to carry out grouping at least a portion of the pixels of the microscopic image data to form one or more pixels groups. The processor is further adapted to carry out calculating, for each of the pixel groups, probabilistic group classification data depending on at least a portion of the pixel classification data of the pixels of the respective group. For one or more of the object classes and for each of the pixel groups, the probabilistic group classification data are indicative of a probability that the respective group shows at least a portion of an object of the respective object class.

Embodiments of the present disclosure provide a computer readable medium having stored thereon the computer program element described in the previous paragraph.

DETAILED DESCRIPTION OF EMBODIMENTS

Figure 1:
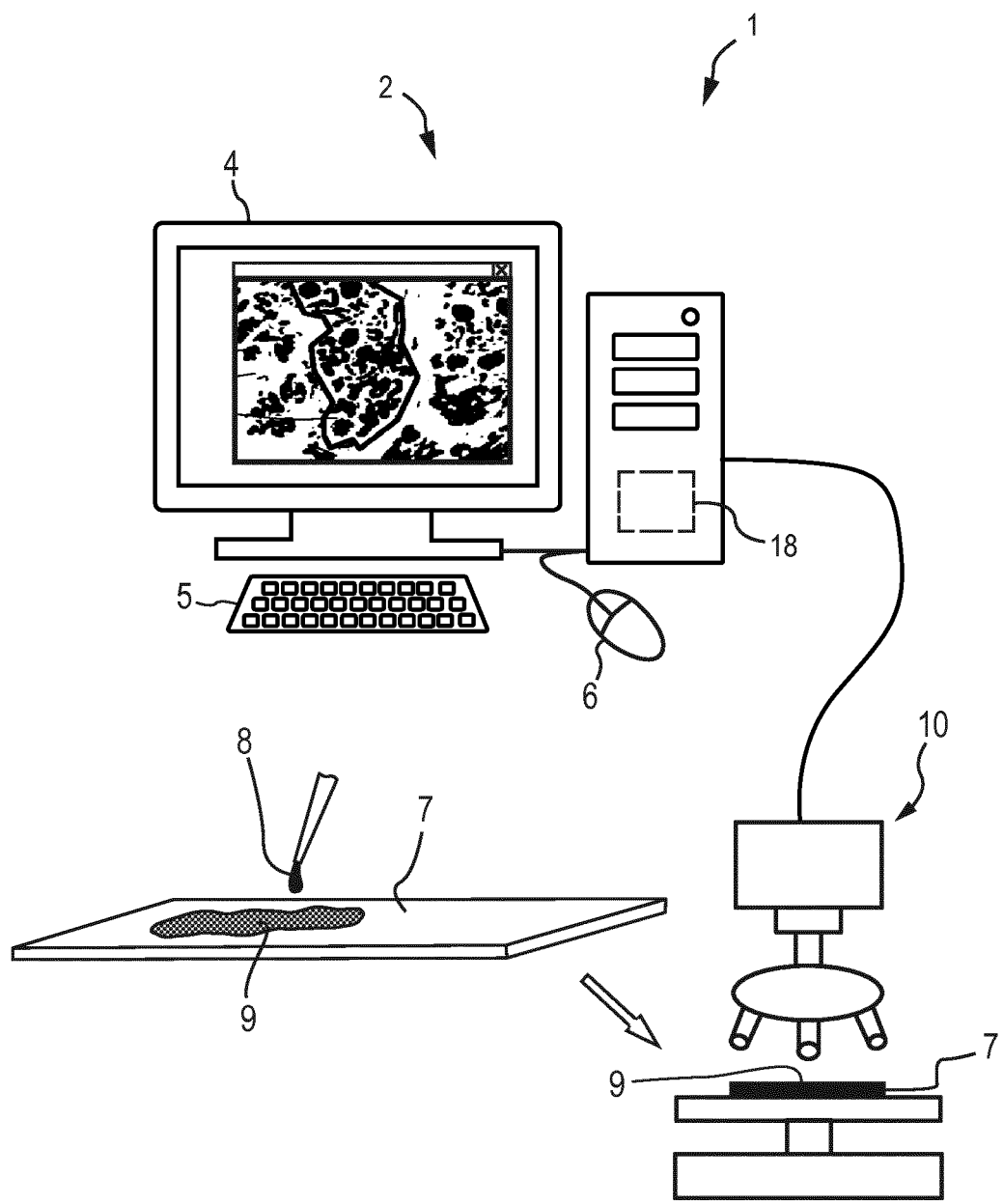
FIG. 1 is a schematic illustration of a system for analysis of microscopic image data according to an exemplary embodiment.

FIG. 1 schematically illustrates a system 1 for analysis of microscopic data according to an exemplary embodiment. The system 1 includes a data processing system 2 which is configured as a stand-alone computer. However, it is also conceivable that the data processing system 2 is configured as a distributed computer system. The data processing system 2 includes a display device 4, and input devices, such as a keyboard 5 and a computer mouse 6 allowing user interaction via user interface of the data processing system 2, which may be configured as a graphical user interface.

The data processing system 2 is configured to read microscopic image data generated using an image acquisition unit 10. In the exemplary embodiment, the image acquisition unit 10 is a microscope slide scanner, such as a whole slide scanner, which is configured to acquire an image of an object 9 which includes cells and which is deposited on a microscope slide 7. The object 9 may be a tissue slice taken from biopsy or resection material or which is obtained using another invasive or non-invasive procedure. Therefore, the system 1 may be used for inspection of histopathological images, in particular for nucleus detection in histopathological images. It is also conceivable that the object 9 is a smear such as a Pap smear which is prepared on the microscope slide 7.

It is to be understood that the invention is not limited to slide scanners. It is also conceivable that other types of microscope systems are used for acquiring the image data. The image data may include greyscale image data and/or color image data.

As is further illustrated in FIG. 1, before the image is acquired, the object 9 is stained using a stain, such as for example H&E stain, in order to be able to distinguish between cells with different morphological appearance. Additionally or alternatively, it is also conceivable that other stains are used, such as immunohistochemical stain to discriminate between cells having a similar appearance. The stain may be selected depending on the one or more object classes which are used to classify the image data as is described further below.

The image data which have been acquired using the image acquisition unit 10 are analyzed by a classifier 18 of the data processing system 2 to perform a pixelwise classification of the image which yields, for each of the pixels, a probability value indicating the probability that the pixel is part of an object of a predefined object class. In the exemplary embodiment, the predefined object class represents cell nuclei of all kinds. Therefore, for each pixel of the image data, the classifier 18 calculates a probability value which indicates that the respective pixel represents a portion of a cell nucleus. It also conceivable that the classifier 18 of the data processing system 2 is configured to perform a pixelwise classification into a plurality of predefined classes (rather than into a single class), such as immune cell nuclei and tumor cell nuclei.

It is to be noted that the classes are not limited to classes of cell nuclei. It is further conceivable that additionally or alternatively the classifier 18 classifies into one or more classes of tissue portions (such as tumor tissue portions and non-tumor tissue portions), classes of cells (such as cells of all kinds, tumor cells and immune cells) and/or classes of cells clusters (such as cell clusters of any kind, tumor cell clusters and immune cell clusters).

The classifier 18 of the data processing system is a supervised learning classifier 18 which may be implemented using an artificial neural network. It has been shown that conventional training procedures for supervised learning systems is inefficient, since these procedures are cumbersome and time-consuming and therefore costly. Specifically, performing a manual annotation of a detailed contour around the nucleus boundary requires approximately 10 mouse clicks per nucleus and today's nucleus detection algorithms typically require a large number of nucleus annotations ranging approximately between 10,000 and 100,000. Generally, deep learning requires good quality annotated data for training. The bigger the annotated data set, the better is the achieved performance improvement.

It has further been shown that manually prepared annotated data sets result in inconsistent annotations. By way of example, some users mark the nucleus' extent by indicating the boundary pixels of the nucleus while others use square regions around the nucleus. This results in inconsistent annotated data sets so that the result achieved through the training processes strongly depends on the user who is training the system.

In view of the foregoing, the inventors have found that it is possible to provide a system and a method for efficient training of classifiers which are more time efficient and less dependent on subjective identification and interpretation of the image data by human users. Specifically, the inventors have found that it is possible to use the data processing system 2 to interactively generate a comparatively large annotated dataset for training the classifier in an efficient manner.

Figure 2:
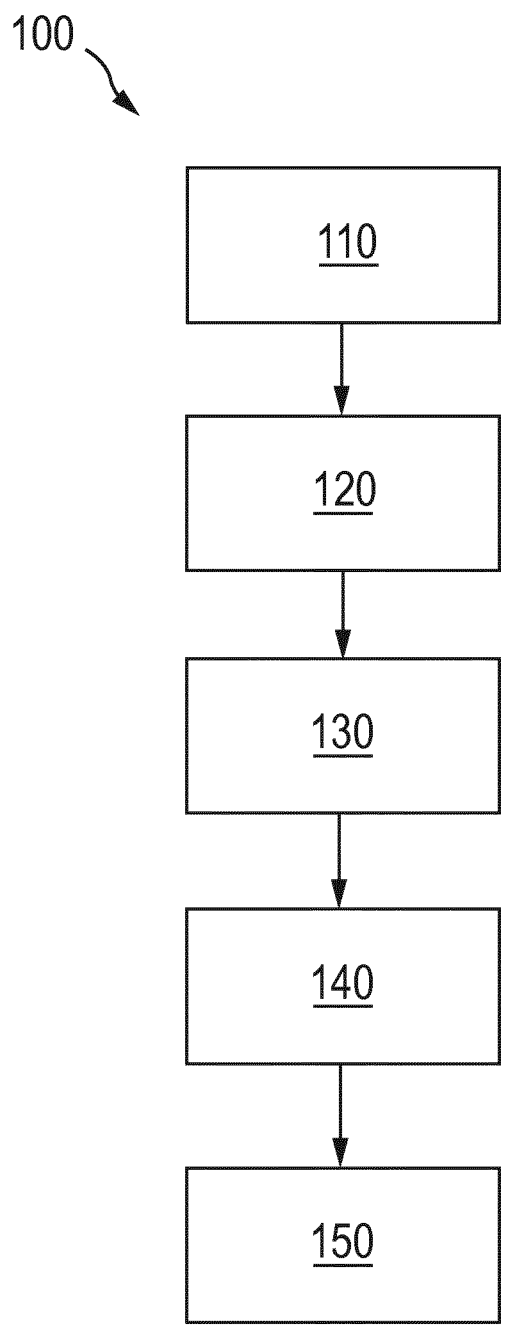
FIG. 2 is a flowchart schematically illustrating an exemplary method for analyzing the microscopic image data, wherein the method is performed using the system according to the exemplary embodiment shown in FIG. 1.

FIG. 2 is a flow chart illustrating an exemplary method 100 which is performed using the system 1 which is illustrated in FIG. 1. In a first step, the microscopic image data are generated 110 using the image acquisition unit 10 (shown in FIG. 1). The image data are input to the classifier which is implemented by the data processing system and which is configured to perform the pixelwise classification as described above.

Figure 3:
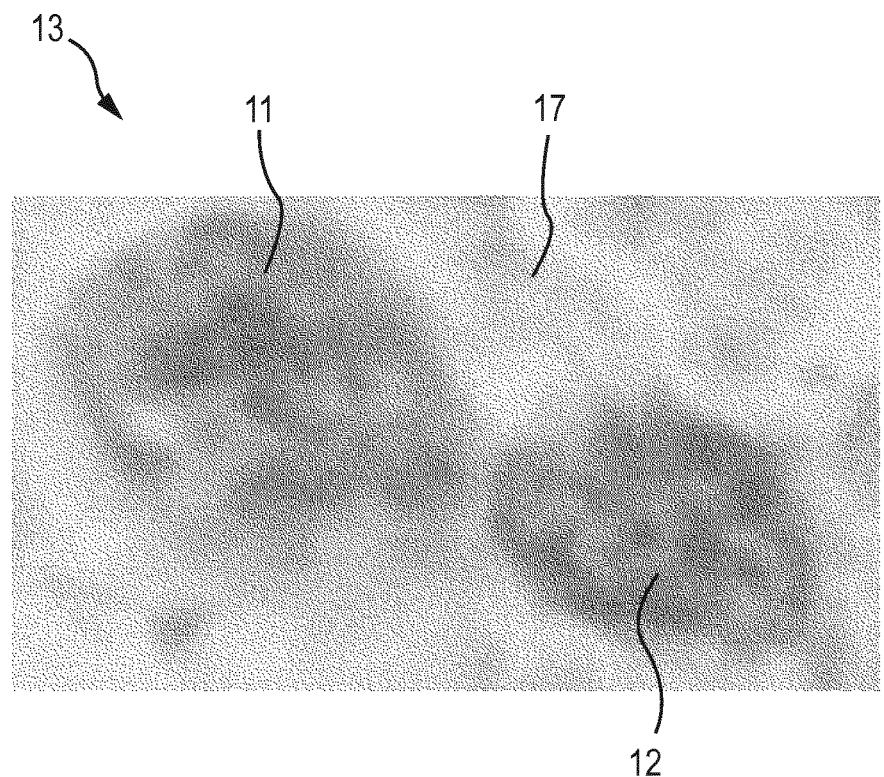
FIG. 3 is a portion of microscopic image data which is analyzed using the system according to the exemplary embodiment shown in FIG. 1 and the exemplary method shown in FIG. 2.

An example of a portion of the microscopic image data which is input to the classifier 18 is depicted in FIG. 3 and shows two image structures 11 and 12, each of which representing a cell nucleus which has been stained using H&E staining. The portions of the cell membranes which are located between the cell nuclei are not delineated by the H&E stain. Based on the image data, the trained eye of the user recognizes the cell nuclei by their morphology, such as size, shape and/or texture. By way of example, H&E stained samples may exhibit a pattern within cell nuclei which is caused by chromatin.

As described above, the classifier which is implemented in the data processing system is configured to read the microscopic image data as input data and to assign to each pixel of the input image data, a probability value which indicates a probability that the pixel forms part of a cell nucleus. In other words, the classifier 18 performs semantic segmentation of the microscopic image data by determining a probabilistic classification for each of the pixels. In the exemplary embodiment, this is performed using an artificial neural network in which an image (color RGB-image or greyscale image) is converted into pixelwise class probabilities.

Generally, an artificial neural network includes an input layer, one or more intermediate layers and an output layer. The output layer may include a softmax operation $$\text{Prob}(i) = \text{SoftMax}(Z) = \frac{\exp(Z_i)}{\sum_{i=1}^{K} \exp(Z_i)} \quad \text{Equation (1)}$$

which converts output values $Z_i$ of the layer which immediately precedes the output layer (which is the last dense layer, wherein the dense layer is also denoted as "fully connected layer") into a probability distribution Prob(i) over a plurality of classes i=0, . . . K. K is the number of the classes which is equal to the number of output values $z_i$ (i=0 . . . K) of the layer immediately preceding the output layer. As can be seen from Equation 1 above, the probability distribution Prob(i) is obtained by determining the exponential of the output values $Z_i$ of the last intermediate layer and by normalizing the determined exponential over the classes to ensure that the sum of the values of the probability distribution Prob(i) is 1.

In order to resolve characteristics of the values of the probability distribution Prob(i) for values which are either close to 1 or close to 0, and thereby to facilitate evaluation of the probability distribution Prob(i) (as will be explained in more detail further below), an inverse of the sigmoid function (also denoted as logit function) is applied to the probability distribution Prob(i). The output values of the logit function are clipped to a range, such as the range of −14 to 14, and then linearly mapped to the range between 0 and 1. The range to which the output values of the logit function are clipped is selected depending on the level of details in the classification result which are to be discriminated.

The mapped values are used as probabilistic pixel classification data which, for each of the pixels of the image, are indicative of a probability that the respective pixel is part of an image structure which represents a cell nucleus. In other words, the probabilistic pixel classification data of a pixel is a measure of the uncertainty that the pixel represents a portion of a nucleus.

It is also conceivable that a layer which precedes the output layer (in particular the layer which immediately precedes the output layer) is used to determine the pixel classification data. By way of example, by using the output data of the layer which immediately precedes the output layer, it is possible to omit the normalizing step that is part of the softmax operation shown in Equation 1.

Figure 4A:
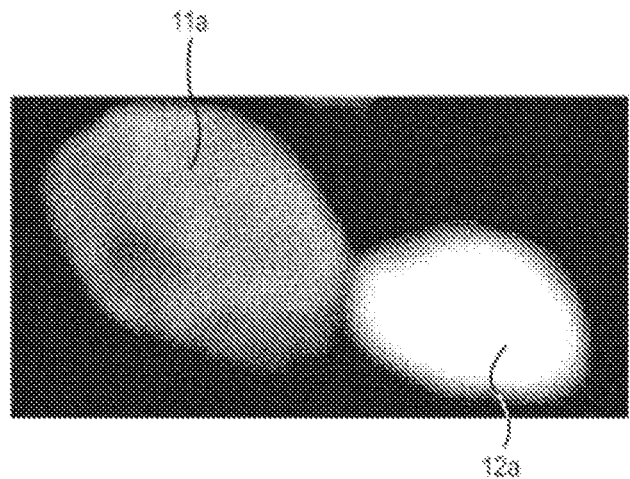
FIG. 4A is a schematic illustration of pixel classification data determined using the system according to the exemplary embodiment shown in FIG. 1 and the exemplary method shown in FIG. 2.
Figure 4B:
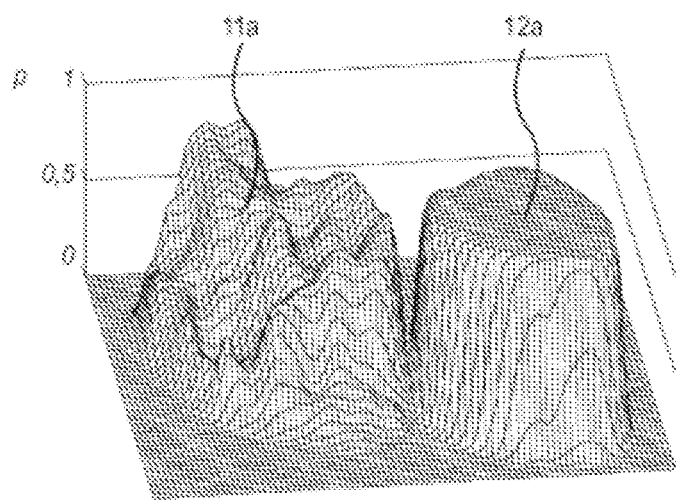
FIG. 4B is a three-dimensional surface diagram illustrating the pixel classification data which are also shown in FIG. 4A.

Accordingly, the exemplary method 100 (shown in FIG. 2) includes the step of generating 120, for each pixel in the input image, pixel classification data to obtain a map of probability values which is depicted in FIG. 4A. A corresponding three-dimensional surface map is shown in FIG. 4B. As can be seen from FIG. 4B, for each pixel of the image which is shown in FIG. 3, the pixel classification data includes a probability value which is in the range of between 0 and 1. This leads to structures 11a and 12a in FIGS. 4A and 4B which correspond to the image structures 11 and 12 which are visible in the image data shown in FIG. 3.

As can further be seen from FIGS. 4A and 4B, the classifier is sufficiently trained to recognize that the image structure 12 of the image data shown in FIG. 3 is a cell nucleus, since the probability values which form the structure 12a of FIGS. 4A and 4B form a plateau over a predominant portion of the structure. On the other hand, as can also be seen from FIGS. 4A and 4B, the classifier is not sufficiently trained to recognize that the image structure 11 also represents a cell nucleus, since in the structure 11a of FIGS. 4A and 4B, the probability values are significantly lower than 1, mostly ranging between 0.3 and 0.8.

The recognition accuracy of the classifier for recognizing the image structure 11 can be increased by generating an annotated data set. The annotated data set includes the pixel data values of the image structure 11 and a classification label which indicates whether or not the image structure 11 is a cell nucleus. On the other hand, it is not necessary to include the pixel data values of the image structure 12 to the annotated data set, since this image structure is already classified by the classifier as a cell nucleus with a sufficiently high recognition accuracy.

The inventors have found that the pixel classification data are helpful for automatically or interactively (i.e. based on user intervention) detecting the boundaries of the nuclei. This can be seen by comparing the image structure 11 shown in FIG. 3 with the corresponding structure 11a shown in FIGS. 4A and 4B. More specifically, in FIG. 3, the intensity variations in the image structure 11 which are caused by the chromatin pattern in the nucleus, together with the intensity variations in the background 17 of the image portion 13 make it difficult to determine the boundary of the nucleus represented by the image structure 11. On the other hand, using the probability values depicted in FIGS. 4A and 4B, it is much easier to determine the boundary of the nucleus which is represented by the structure 11a.

Returning to FIG. 2, depending on the pixel classification data, which are illustrated in FIGS. 4A and 4B, the data processing system performs the step of grouping 130 a portion of the pixels to form a plurality of pixel groups so that each of the pixel groups has an increased probability of representing a nucleus, compared to the background. Therefore, the pixel groups may, but need not necessarily, represent a nucleus. The pixel groups may be formed so that the pixel groups represent pixel clusters (i.e. a non-divided image region) or substantially represent pixel clusters. Further, the pixel groups may be formed so that the pixel clusters represent image regions without holes.

The pixel groups may be formed using image processing operations, such as image segmentation using thresholding and/or an edge detection filter. The pixel groups may be formed using a learning system or a non-learning system.

It has been shown that forming the pixel groups depending on the pixel classification data yield more reliable results compared to segmentation operations which segment the microscopic image data and which tend to fail when the objects or the background have complex shapes or complex variations in intensity values or color.

The formation of the pixel groups may include applying to the pixel classification data a noise suppression filter, such as Gaussian smoothing. A local maximum of the probability values may be determined, for example, after the noise suppression filter has been applied. Then, a pixel cluster is formed which includes the local maximum, and all those pixels which have a probability greater than a predefined threshold value and which form a pixel cluster with the local maximum. By way of example, the threshold may be in a range of between 0.3 and 0.8 or in a range of between 0.4 and 0.6, such as 0.5. Further, the formation of the pixel groups may include a morphological hole filling operation, which may be applied to the identified pixel clusters. Thereby, pixel groups without holes can be obtained.

Additionally or alternatively, further algorithms may be applied for forming the pixel groups, which may include but are not limited to: active contour operations, watershed operations, level set operations, and maximally stable extremal regions. These algorithms may use the identified local maxima in probability.

It is also conceivable that the the pixel clusters are determined further depending on the image data. By way of example, the data processing system may apply color deconvolution to the image data to determine a map representing the haematoxylin absorption. Then, a weighted sum $$s_{i,j} = \alpha * b_{i,j} + (\alpha - 1) * c_{i,j} \qquad \text{Equation (2)}$$

may be calculated with a being a weighing factor in the range of between 0 and 1, $b_{i,j}$ being pixel data values of the microscope image (e.g. after application of a noise reduction filter), $c_{i,j}$ being the map representing the hematoxylin absorption and i and j indicating the row and column of the pixel data values and the haematoxylin absorption map.

Based on the pixel classification data which are shown in FIGS. 4A and 4B, the data processing system forms two pixel groups, each of which being a pixel cluster and representing one of the cell nuclei.

As a next step in the exemplary method which is shown in FIG. 2, the data processing system calculates 140, for each of the pixel groups, probabilistic group classification data depending on at least a portion of the pixel classification data of the pixels of the respective group. In other words, in the example which is illustrated in FIGS. 3 to 4B, for each of the pixel groups which correspond to the image structures 11 and 12 in the image data of FIG. 3, the data processing system calculates a probability value which indicates a probability that the respective pixel group is a cell nucleus. Thereby, for example, for the image regions 11 and 12, two probability values are obtained. In the exemplary embodiment, the probabilistic group classification data is a mean value of the pixel classification data (i.e. a mean value of the probability values) of the pixels of the respective pixel group. The data processing system may be configured to exclude pixels from the determination of the group classification data which represent a transition from an interior of the pixel group to a surrounding image region which does not represent a nucleus. It has been shown that this leads to higher recognition accuracies after the training procedure.

Since, as can be seen from FIG. 4B, a predominant portion of the probability values of the pixel classification data of the structure 12a which corresponds to the image region 12 in FIG. 3 have values close to 1, the probability value of the group classification data is also close to 1. On the other hand, as can also be seen from FIG. 4B, the pixels corresponding to the image region 11 have probability values much lower than 1. Therefore, the corresponding probability value of the group classification data has a probability value which is much lower than 1, thereby indicating that the classifier is not sufficiently trained to recognize the image region 11 as representing the cell nucleus.

As is explained in the following, the group classification data can be used in an efficient manner to perform the step of generating 150 (shown in FIG. 2) an annotated dataset for training the classifier 18 (shown in FIG. 1) of the data processing system 2. In the exemplary embodiment, the annotated data set is generated interactively, i.e. using user intervention via a graphical user interface of the data processing system. However, it is also conceivable that the annotated data set is generated by the data processing system automatically (i.e. without user intervention).

Figure 5:
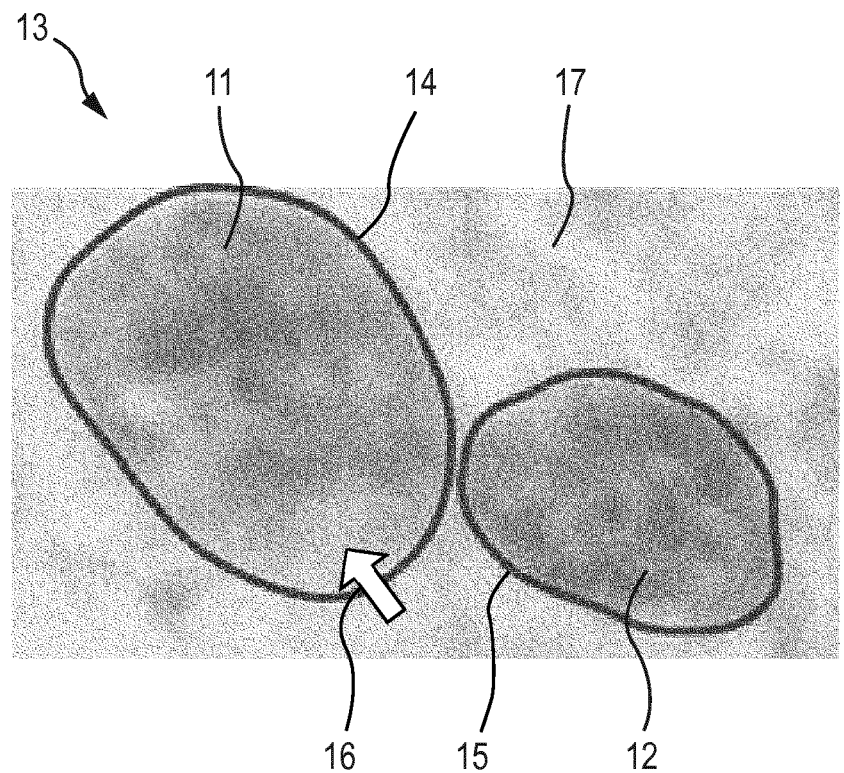
FIG. 5 shows the portion of the image data of FIG. 3 and visually perceptible indicators which are displayed to the user using a graphical interface of the system according to the exemplary embodiment shown in FIG. 1A.

The interactive generation of the annotated data set is illustrated in FIG. 5. The data processing system displays on the display device 4 (shown in FIG. 1) the image portion 13 showing the image regions 11 and 12 representing two cell nuclei. For simplicity of illustration, only the image portion 13 is shown in FIG. 5. The data processing system may display on the display device an image showing numerous cell nuclei, allowing the user to generate a comparatively large annotated data set within a short period of time.

Further, the data processing system displays, for each of the pixel groups, a visually perceptible indicator 14, 15 which is indicative of the extent of the respective pixel group. In the exemplary embodiment, for each of the pixel groups, the indicator surrounds the pixels of the respective group. However, other configurations of the indicator are conceivable, such as a transparent overlay image which covers the pixel group and which has the same extent as the pixel group.

The indicators 14, 15 allow the user to quickly recognize that the data processing system has identified two pixel groups, each of which having a particular probability of representing a cell nucleus.

The data processing system is further configured so that for each of the pixel groups, the visually perceptible indicator is indicative of the group classification data generated by the data processing system for each of the pixel groups. In the exemplary embodiment, for each of the pixel groups, a color of the respective indicator 14, 15 is indicative of the probability value of the group classification data. By way of example, pixel groups surrounded by a white indicator indicate group classification data representing a high probability value. Pixel groups with red, orange or yellow indicator indicate pixel groups having classification data representing a lower probability value and which therefore correspond to pixel groups that are potentially more valuable for annotation.

Additionally or alternatively, it is conceivable that the shape of the indicator, such as the line type (i.e. line types such as solid, dashed and dotted) is indicative of the probability value of the group classification data.

Since the indicators 14 and 15 are indicative of the group classification data, it is possible for the user to easily identify pixel groups which have a medium probability value and for which the classifier is thereby not sufficiently trained to classify them either as representing a nucleus or as not representing a nucleus. If these pixel groups are included in the annotated data set together with a user-generated classification label, which indicates whether the pixel group represents or does not represent a nucleus, the recognition accuracy of the classifier can be improved.

Since the pixel groups are displayed together with the indicators 14 and 15, the user can assess, based on the morphology of the pixel groups, whether or not the respective pixel group represents a cell nucleus.

The user interface of the data processing system is further configured to allow the user to select one or more pixel groups which are to be included in the annotated data set and to generate, for each of the selected pixel groups, a classification label indicating whether or not the pixel group represents a cell nucleus. In the exemplary embodiment, the graphical user interface is configured to allow the user to select one or more of the pixel groups by using the mouse pointer 16 of the computer mouse. By way of example, after the mouse pointer 16 has been positioned over a pixel group, it is possible for the user to interact with the pixel group in order to generate the classification label. The interaction may be performed by selecting an entry of a drop-down list which is displayed after the pixel group has been selected or by toggling between different options using a key of the keyboard. In a same manner, the data processing system may be configured to allow the user to remove pixel groups from the annotated data set.

The data processing system is configured so that the indicators 14 and 15 indicate whether the corresponding pixel group has been added to the annotated data set. By way of example, after the pixel group has been selected and the classification label has been generated, the color of the indicator changes to green. The data processing system may further be configured so that the indicators 14 and 15 indicate whether the pixel group has been labeled by the user as being a nucleus or as not being a nucleus.

The data processing system may further be configured to allow the user to add and/or remove pixels from one or more selected pixel groups. By way of example, the user, after having selected at least one of the pixel groups, may adapt the threshold value which is used to determine the pixel group, as has been described above. The threshold value may be adapted by scrolling the mouse wheel.

Additionally or alternatively, the data processing system may further be configured to allow the user to create new pixel groups and/or to delete pixel groups. By way of example, by positioning the mouse pointer 16 on a pixel which is not part of a pixel group and by providing user input which is indicative of a threshold value, the data processing system may generate a new pixel group by thresholding probability data around the position of the computer mouse 16. The thresholding may be performed after a noise suppression filter has been applied to the probability values. The threshold value may, for example, be controllable by scrolling the mouse wheel.

Then, the data processing system generates the annotated data set for training the classifier based on the microscopic image data values of the labeled pixel groups and the associated classification labels. The annotated data set is then used for training the classifier 18 (shown in FIG. 1) which is implemented in the data processing system to obtain a higher recognition accuracy for recognizing cell nuclei.

In the exemplary embodiment described above, the pixel classification data which are used for forming the pixel groups are generated using the classifier which is later trained using the annotated data set. The initial training of the classifier (i.e. before the training using the interactively generated annotated data set is performed) may be performed based on a small number of manually prepared annotated data sets and/or using publicly available annotated data sets. However, as an alternative exemplary embodiment, it is also conceivable that the classifier used for generating the pixel classification data is a second classifier, which is implemented separately from the classifier which is trained using the annotated data set. The second classifier may be a supervised learning system, an unsupervised learning system or a non-learning system.

Thereby, a method and a system is provided which allow efficient generation of an annotated data set. Further, it has been shown, saying the user is provided with groups and group classification data are determined by the data processing system, the dependency of the annotated data set is less dependent on the individual user.

The above embodiments as described are only illustrative, and not intended to limit the technique approaches of the present invention. Although the present invention is described in details referring to the preferable embodiments, those skilled in the art will understand that the technique approaches of the present invention can be modified or equally displaced without departing from the protective scope of the claims of the present invention. In particular, although the invention has been described based on a projection radiograph, it can be applied to any imaging technique which results in a projection image. In the claims, the word "comprising" does not exclude other elements or steps, and the indefinite article "a" or "an" does not exclude a plurality. Any reference signs in the claims should not be construed as limiting the scope.

The invention claimed is:

1. A system for analysis of microscopic image data, the system comprising a data processing system;
   wherein the data processing system is configured to:
   read or generate pixel classification data for each of a plurality of pixels of the microscopic image data, wherein the pixel classification data comprise, for each of the plurality of pixels of the microscopic image data, binary or probabilistic classification data for classifying the pixel into one or more object classes of predefined objects which are shown by the image;
   group at least a portion of the pixels of the microscopic image data to form one or more pixels groups; and
   calculate, for each of the pixel groups, probabilistic group classification data depending on at least a portion of the pixel classification data of the pixels of the respective group;
   wherein for one or more of the object classes and for each of the pixel groups, the probabilistic group classification data are indicative of a probability that the respective group shows at least a portion of an object of the respective object class.

2. The system of claim 1, wherein the data processing system comprises a user interface which is configured for interactive generation of an annotated data set for training a classifier using the probabilistic group classification data.

3. The system of claim 2, wherein the interactive generation of the annotated data set comprises receiving user input which is indicative of a classification label for one of the pixel groups, wherein the classification label assigns the pixel group to one or more of the object classes or indicates that the pixel group does not represent an object of any of the predefined object classes.

4. The system of claim 3, wherein the data processing system is configured to generate the pixel classification data using a classifier and to perform supervised training of the classifier using the pixels of at least a portion of the pixel groups.

5. The system of claim 2, wherein the data processing system is configured to display, using the user interface of the data processing system, one or more of the pixel groups and for each of the displayed pixel groups a visually perceptible indicator which is generated depending on the probabilistic group classification data of the respective pixel group.

6. The system of claim 5, wherein the indicator is indicative of an extent of the pixel group.

7. The system of claim 6, wherein the data processing system is configured to generate the pixel classification data using a classifier and to perform supervised training of the classifier using the pixels of at least a portion of the pixel groups.

8. The system of claim 5, wherein the data processing system is configured to generate the pixel classification data using a classifier and to perform supervised training of the classifier using the pixels of at least a portion of the pixel groups.

9. The system of claim 2, wherein the data processing system is configured to generate the pixel classification data using a classifier and to perform supervised training of the classifier using the pixels of at least a portion of the pixel groups.

10. The system of claim 1, wherein the one or more pixel groups are formed depending on at least a portion of the pixel classification data.

11. The system of claim 10, wherein the one or more pixel groups are formed using a threshold value for the pixel classification data.

12. The system of claim 10, wherein the data processing system is configured to generate the pixel classification data using a classifier and to perform supervised training of the classifier using the pixels of at least a portion of the pixel groups.

13. The system of claim 1, wherein the data processing system is configured to generate the pixel classification data using a classifier and to perform supervised training of the classifier using the pixels of at least a portion of the pixel groups.

14. The system of claim 1, wherein each of the pixel groups substantially represents a pixel cluster.

15. The system of claim 1, wherein the data processing system is further configured to generate the pixel classification data depending on data generated using a classifier executed by the data processing system, wherein the data generated using the classifier comprise output data outputted by a layer of an artificial neural network of the classifier.

16. System of claim 15, wherein the generation of the pixel classification data comprises applying a logit function to the output data and/or to data generated using the output data.

17. The system of claim 1, wherein for each of the pixel groups, the corresponding probabilistic group classification data are determined depending on a mean value of the pixel classification data of at least a portion of the pixels of the respective pixel group.

18. A method for analysis of microscopic image data using a data processing system, the method comprising:
    reading or generating pixel classification data for each of a plurality of pixels of the microscopic image data, wherein the pixel classification data comprise, for each of the plurality of pixels of the microscopic image data, binary or probabilistic classification data for classifying the pixel into one or more object classes of predefined objects which are shown by the image;
    grouping at least a portion of the pixels of the microscopic image data to form one or more pixels groups; and
    calculating, for each of the pixel groups, probabilistic group classification data depending on at least a portion of the pixel classification data of the pixels of the respective group;
    wherein for one or more of the object classes and for each of the pixel groups, the probabilistic group classification data are indicative of a probability that the respective group shows at least a portion of an object of the respective object class.

19. A non-transitory computer readable medium comprising a program element encoded therein for analysis of microscopic image data using a data processing system, wherein the program element, when being executed by a processor of the data processing system, is adapted to carry out:

reading or generating pixel classification data for each of a plurality of pixels of the microscopic image data, wherein the pixel classification data comprise, for each of the plurality of pixels of the microscopic image data, binary or probabilistic classification data for classifying the pixel into one or more object classes of predefined objects which are shown by the image;

grouping at least a portion of the pixels of the microscopic image data to form one or more pixels groups; and calculating, for each of the pixel groups, probabilistic group classification data depending on at least a portion of the pixel classification data of the pixels of the respective group;

wherein for one or more of the object classes and for each of the pixel groups, the probabilistic group classification data are indicative of a probability that the respective group shows at least a portion of an object of the respective object class.

* * * * *